United States Patent [19]

Schönafinger et al.

[11] Patent Number: 4,937,244
[45] Date of Patent: Jun. 26, 1990

[54] SUBSTITUTED 3-AMINOSYDNONIMINES, PROCESSES FOR THEIR PREPARATION AND THEIR USE

[75] Inventors: Karl Schönafinger, Alzenau; Rudi Beyerle, Frankfurt, both of Fed. Rep. of Germany

[73] Assignee: Cassella Aktiengesellschaft, Frankfurt, Fed. Rep. of Germany

[21] Appl. No.: 238,456

[22] Filed: Aug. 3, 1988

[30] Foreign Application Priority Data

Sep. 24, 1987 [DE] Fed. Rep. of Germany ....... 3732174

[51] Int. Cl.$^5$ .................. A61K 31/495; A61K 31/41; A61K 31/445; A61K 31/535; A61K 31/54; C07D 413/04

[52] U.S. Cl. .................. 514/252; 514/227.8; 514/236.2; 514/326; 514/364; 544/60; 544/138; 544/367; 546/209; 548/125

[58] Field of Search ................. 546/209, 289; 514/326, 514/227.8, 236.2, 252, 364; 544/138, 60, 367; 548/125

[56] References Cited

U.S. PATENT DOCUMENTS

| | | | |
|---|---|---|---|
| 3,812,128 | 5/1974 | Masuda et al. | 548/125 |
| 3,833,580 | 9/1974 | Grotz et al. | 548/125 |
| 3,833,589 | 9/1974 | Simpson | 548/125 |
| 4,245,100 | 1/1981 | Kholodov et al. | 548/125 |
| 4,277,609 | 7/1981 | Stein | 548/125 |
| 4,289,885 | 9/1981 | Stein | 546/209 |
| 4,301,285 | 11/1981 | Stein | 546/209 |
| 4,324,897 | 4/1982 | Stein | 548/125 |
| 4,371,539 | 2/1980 | Stein | 548/125 |
| 4,371,697 | 2/1983 | Stein | 548/125 |
| 4,421,754 | 12/1983 | Hidaka et al. | 548/125 |
| 4,430,342 | 2/1984 | Hidaka et al. | 548/125 |
| 4,436,743 | 3/1984 | Schonafinper et al. | 548/125 |
| 4,446,322 | 5/1984 | Stein | 548/125 |

OTHER PUBLICATIONS

Schmidt, CA 100-56858m (1984).

*Primary Examiner*—Cecilia Shen
*Attorney, Agent, or Firm*—Perman & Green

[57] ABSTRACT

Substituted 3-aminosydnonimines of the formula I

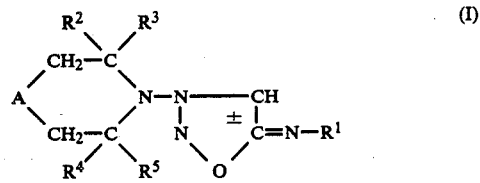

and their pharmacologically acceptable acid addition salts wherein
A denotes, for example, —CH$_2$—,
R$^1$ denotes hydrogen or the radical —COR$^7$,
R$^2$, R$^3$, R$^4$ and R$^5$ denote alkyl with 1 to 4 C atoms and
R$^7$ denotes, for example, an aliphatic radical and 1 to 4 C atoms, are prepared by cyclization of a compound of the formula II

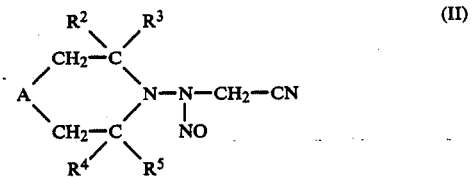

and if appropriate subsequent acylation and have useful pharmacological properties. The invention includes pharmaceutical preparations containing the present compounds, and the use thereof for treating patients having cardiovascular ailments.

9 Claims, No Drawings

SUBSTITUTED 3-AMINOSYDNONIMINES, PROCESSES FOR THEIR PREPARATION AND THEIR USE

The invention relates to pharmacologically active substituted 3-aminosydnonimines of the general formula I

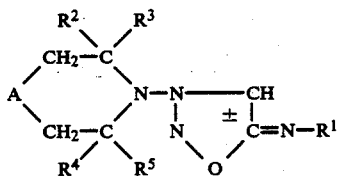

and their pharmacologically acceptable acid addition salts, wherein

A denotes the radical —CH$_2$—, —O—, —S(O)$_n$—, —N(R$^6$)— or a direct bond;

R$^1$ denotes hydrogen or the radical —COR$^7$;

R$^2$, R$^3$, R$^4$ and R$^5$ denote alkyl with 1 to 4 C atoms; n the number 0, 1 or 2, R$^6$ denotes alkyl with 1 to 4 C atoms; hydroxyalkyl with 2 to 4 C atoms; or phenylalkyl with 1 to 4 C atoms in the alkyl radical, R$^7$ denotes an aliphatic radical which has 1 to 4 C atoms and can also be substituted by alkoxy with 1 to 3 C atoms; a cycloaliphatic radical with 5 to 7 C atoms; a bicycloaliphatic radical with 7 to 14 C atoms; a tricycloaliphatic radical with 7 to 16 C atoms; an alkoxy radical with 1 to 6 C atoms; an aryloxy radical with 6 to 10 C atoms; an alkoxycarbonyl radical with a total of 2 to 7 C atoms; an aryl radical with 6 to 10 C atoms; or an aryl radical which has 6 to 10 C atoms and is mono-, di- or trisubstituted by 1 to 3 halogen atoms and/or 1 to 3 alkyl radicals with 1 to 3 C atoms and/or 1 to 3 alkoxy radicals with 1 to 3 C atoms and/or 1 or 2 nitro groups; and n denotes the number 0, 1 or 2.

The invention furthermore relates to a process for the preparation of the compounds according to the invention and their use.

If A denotes one of the radicals —CH$_2$—, —O—, —S(O)$_n$, or —N(R$^6$)—, the radical of a heterocyclic 6-ring with one hetero atom (N) or with two hetero atoms (N,O or N,S or N,N), which is tetraalkylated in the manner described, is in the 3-position of the sydnonimine. If A denotes a direct bond, a pyrrolidine radical which is tetraalkylated in the 2,2,5,5-position is in the 3-position of the sydnonimine.

The number 2 is preferred for n.

Of the divalent radicals A, the preferred radicals are —CH$_2$—, —O— and —N(R$^6$)—.

Hydrogen is preferred for R$^1$.

Aliphatic radicals, alkyl radicals, hydroxyalkyl radicals and alkoxy radicals can be straight-chain or branched. This also applies if they occur as substituents of other radicals, for example as substituents for aryl radicals, or in association with other radicals, for example as phenalkyl or as alkoxycarbonyl.

The alkyl radicals R$^2$, R$^3$, R$^4$ and R$^5$ can be identical or different. As a rule, they are all the same. Straight-chain alkyl radicals are above all suitable for R$^2$ to R$^5$. The four radicals R$^2$, R$^3$, R$^4$ and R$^5$ particularly preferably all denote methyl.

Alkyl with 1 to 4 C atoms is preferred for R$^6$

Alkyl radicals with 1 to 4 C atoms are particularly suitable as aliphatic radicals R$^7$. The methoxymethyl radical may be mentioned in particular as an aliphatic radical R$^7$ which is substituted by alkoxy with 1 to 3 C atoms. Cycloalkyl radicals with 5 to 7 C atoms, in particular cyclopentyl and preferably cyclohexyl, are above all suitable as a cycloaliphatic radical R$^7$. 2,6,6-Trimethylbicyclo[3.1.1]heptan-3-yl (=pinan-3-yl) is particularly suitable as a bicycloaliphatic radical R$^7$. Tricyclo[3.3.1.1$^{3,7}$]decan-1-yl (=adamantanyl) is particularly suitable as a tricycloaliphatic radical R$^7$. Methoxy and ethoxy radicals are particularly suitable as alkoxy radicals R$^7$. The ethoxycarbonyl radical is particularly suitable as an alkoxycarbonyl radical R$^7$. α- or β-naphthyl radicals, for example, but in particular the phenyl radical, may be mentioned as aryl radicals R$^7$. α- or β-naphthoxy radicals, for example, but in particular the phenoxy radical, may be mentioned as aryloxy radicals R$^7$. The aryl radicals R$^7$ can be mono-, di- or trisubstituted, but even with trisubstitution only a maximum of 2 nitro groups may be present, examples being 2-methyl-4,6-dinitrophenyl and 2-chloro-6-methyl-4-nitrophenyl. Chlorine and bromine atoms, for example, are suitable halogen substituents for the aryl radicals. Substituted aryl radicals R$^7$ which may be mentioned in particular are: methylphenyl (=tolyl), nitrophenyl and chlorophenyl, in particular 4-nitrophenyl and 4-chlorophenyl.

The following are preferred for R$^7$ alkyl radicals with to 4 C atoms, alkoxy radicals with 1 or 2 C atoms, cycloalkyl radicals with 5 to 7 C atoms and phenyl. The following are especially preferred: methyl, ethyl, isopropyl, ethoxy, cyclohexyl and phenyl.

A compound of the general formula I can be prepared by a process in which a compound of the general formula II

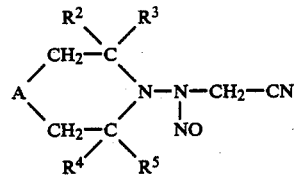

wherein A, R$^2$, R$^3$, R$^4$ and R$^5$ have the meanings already given, is cyclized to a compound of the general formula Ia

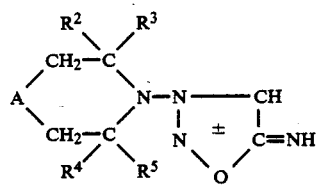

and this compound or an acid addition salt thereof, in the case where a compound of the formula I with R$^1$=—COR$^7$ is to be prepared, is acylated with an acylating agent which introduces the radical —COR$^7$, and if appropriate the compound thus obtained is converted into a pharmacologically acceptable acid addition salt.

The cyclization of the compound II to give the compound Ia is carried out in a suitable organic or inorganic solvent or dispersing agent with the addition of a cyclizing agent, usually at temperatures from 0° to 40° C., preferably at 0° to 20° C. Suitable cyclizing agents are those which establish a pH of less than 3 in aqueous solution, that is to say, for example, mineral acids, such as sulphuric, nitric or phosphoric acid or preferably hydrogen chloride, but also strong organic acids, such as trifluoroacetic acid. The corresponding acid addition salt of the compound Ia is usually obtained in the cyclization.

Examples of suitable solvents or dispersing agents are alcohols, in particular those with 1 to 6 C atoms, preferably those with 1 to 4 C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those with 2 to 8 C atoms in the molecule, such as, for example, diethyl ether, methylethyl ether, di-n-propyl ether, diisopropyl ether, methyl-n-butyl ether, ethylpropyl ether, dibutyl ether, tetrahydrofuran, 1,4-dioxane, 1,2-dimethoxyethane and bis-β-methoxyethyl ether; oligoethylene glycol dimethyl ethers, such as, for example, pentaglyme; carboxylic acid alkyl esters, in particular those with 3 to 8 C atoms in the molecule, such as, for example, methyl or ethyl acetate; ketones, in particular those with 3 to 10 C atoms in the molecule, such as, for example, acetone, methyl ethyl ketone, methyl n-propyl ketone, diethyl ketone, 2-hexanone, 3-hexanone, di-n-propyl ketone, diisopropyl ketone, diisobutyl ketone, cyclopentanone, cyclohexanone, benzophenone and acetophenone: aliphatic hydrocarbons, such as, for example, hexane, heptane and low- and high-boiling petroleum ethers; cycloaliphatic hydrocarbons, such as, for example, cyclohexane, methylcyclohexane, tetralin and decalin; aromatic hydrocarbons, such as, for example, benzene, toluene, o-, m- and p-xylene and ethylbenzene; halogenated aliphatic or aromatic hydrocarbons, such as, for example, methylene chloride, chloroform, carbon tetrachloride, chlorobenzene, and dichlorobenzene; hexamethylphosphoric acid triamide; sulphoxides, such as, for example, dimethyl sulphoxide; and water. Mixtures of various solvents or dispersing agents, for example water-methanol or, preferably, ethyl acetate-methanol, can also be used.

The compounds of the formula Ia are compounds of the general formula I according to the invention in the case where $R^1$ is hydrogen.

The acylation of the compound of the formula Ia, which can also be in the form of an acid addition salt, for introduction of the radical $R^1=-COR^7$ can be carried out in a manner which is known per se using a suitable acylating agent of the formula III

(III)

wherein X represents a radical which can be split off nucleophilically.

In formula III X denotes, for example, in particular halogen, preferably —Cl or —Br; —OH; —O-alkyl, in particular with 1 to 5 C atoms; —O-aryl, the aryl radical being, in particular, a phenyl radical, which can also be mono- or polysubstituted by alkyl, in particular methyl, and/or nitro and is, for example, a tolyl, dinitrophenyl or nitrophenyl radical; —O—CO—$R^7$; —O—CO—O-alkyl, in particular with 1 to 5 C atoms in the alkyl radical, or the radical, bonded by an N atom, of an azole or benzazole with at least 2 N atoms in the quasi-aromatic 5-membered ring.

The acylation is carried out in a suitable solvent or dispersing agent or in an excess of the acylating agent, advantageously with stirring, at temperatures from 0° C. up to the boiling point of the solvent or acylating agent, in particular from 0° to 50° C., preferably 0° to 20° C.

The molar ratio between the compound of the formula Ia and the acylating agent of the formula III is 1:1. The acylating agent is advantageously used in a slight molar excess. Excesses of up to 30 mol-% are as a rule sufficient, that is to say the molar ratio between the compound of the formula Ia and the acylating agent of the formula III is usually 1: (1 to 1.3), preferably 1: (1 to 1.2).

If an acid is split off in the acylation reaction, it is advantageous to add an acid-scavenger agent, such as, for example, an alkali metal hydroxide, such as, for example, sodium, potassium or lithium hydroxide, a tertiary organic amine, such as, for example, pyridine or triethylamine, an alkali metal carbonate or alkali metal bicarbonate, such as, for example, sodium carbonate or sodium bicarbonate, or an alkali metal salt of a weak organic acid, such as, for example, sodium acetate. Suitable catalysts, such as, for example 4-dimethylaminopyridine, can also be added in the acylation reaction.

The compounds of the formula III are acylating agents and are thus, for example: for X=halogen, acid halides or halogenoformic acid esters, of which acid chloride and chloroformic acid esters are preferred; for —OH, carboxylic acids; for —O-alkyl and —O-aryl esters, of which the tolyl and 2,4-dinitro- or 4-nitrophenyl esters are preferred; for —O—CO—$R^7$, anhydrides; for —O—CO—O-alkyl, mixed carboxylic acid-carbonic acid anhydrides; or heterocyclic amides or azolides, in particular of N,N'-carbonyldiazoles, such as, for example, N,N'-carbonyldiimidazole, 2,2'-carbonyl-di-1,2,3-triazole, 1,1'-carbonyl-di-1,2,4-triazole, N,N'-carbonyl-dipyrazole and 2,2'-carbonyl-ditriazole (compare, for example, H. A. Staab, M. Lucking and F. H. Durr, Chem. Ber. 95, (1962), 1275 et seq., H. A. Staab and A. Mannschreck, Chem. Ber. 95, (1962), 1284 et seq.; H. A. Staab and W. Rohr, "Synthesen mit heterocyclischen Amiden (Azoliden) (Syntheses with Heterocyclic Amides (Azolides))" in "Neuere Methoden der Praparativen Organischen Chemie (Recent Methods of Preparative Organic Chemistry)", volume 5, Verlag Chemie, 1967, page 53 et seq., in particular pages 65 to 69). The acylating agents of the formula III can be prepared by processes which are known per se.

If a carboxylic acid is used as the acylating agent, it is advantageous to add an activating agent, which has the task of increasing or activating the acylation potential of the carboxylic acid or of converting the carboxylic acid into a reactive carboxylic acid derivative of the formula III in situ or preferably shortly before the reaction with the compound of the formula Ia. Suitable activating agents of this type are, for example: N,N'-disubstituted carbodiimides, especially if they contain at least one secondary or tertiary alkyl radical, such as, for example, diisopropyl-, dicyclohexyl- or N methyl-N'-tert.-butyl carbodiimide (compare Methodicum Chimicum, Verlag G. Thieme, Stuttgart, volume 6, (1974), pages 682/683, and Houben-Weyl, Methoden der Org. Chemie (Methods of Organic Chemistry), volume 8, (1952), pages 521/522); carbonic acid derivatives, such as, for example, phosgene and chloroformic acid esters, in particular with 1 to 5 C atoms in the alkyl radical (compare, for example, Tetrahedron Letters 24 (1983), 3365 to 3368); carbonic acid esters, such as, for example, N,N'-disuccinimido carbonate, diphthalimido carbonate, 1,1'-(carbonyldioxy)-dibenzotriazole or di-2-pyridyl carbonate (compare, for example, Tetrahedron Letters, volume 25, no. 43, 4943–4946), if appropriate in the presence of suitable catalysts, such as, for example, 4-dimethylaminopyridine. N,N'-carbonyldiazoles, such as, for example, N,N'-carbonyl-diimidazole, 2,2'-carbonyl-di-1,2,3-triazole, 1,1'-carbonyl-di-1,2,4-triazole, N,N'-carbonyl-dipyrazole, 2,2'-carbonyl-ditetrazole, N,N'-carbonylbenzimidazole or N,N'-carbonylbenztriazole, are furthermore suitable as activating agents (compare, for example, H. A. Staab, M. Lucking and F. H. Durr, loc. cit; H. A. Staab and A. Mannschreck loc. cit.; H. A. Staab and W. Rohr loc. cit). The commercially available N,N'-carbonyl-diimidazole is frequently used as the N,N'-carbonyl-diazole. However, the other N,N'-carbonylazoles are also readily accessible from the particular azole and phosgene.

Suitable activating agents for the carboxylic acid are furthermore: derivatives of oxalic acid, such as, for example, oxalyl chloride, (compare, for example, British Patent Specification No. 2,139,225) or N,N'-oxalyldiazoles, such as, for example, 1,1'-oxalyldi-imidazole, 1,1'-oxalyldi-1,2,4-triazole and 1,1'-oxalyldi-1,2,3,4-tetrazole (compare, for example, Shizuaka Murata, Bull. Chem. Soc. Jap. 57, 3597–3598 (1984)); methylethylphosphinic acid anhydride (compare, for example, German Offenlegungsschrift No. 3,101,427); disphosphorus tetraiodide (Chem. Lett. 1983, 449); dialkyldisulphite (Indian J Chem. 21, 259 (1982)); or other reactive agents.

The acylation of the compound of the formula Ia with the acylating agent III is carried out in a suitable solvent or dispersing agent or in an excess of the acylating agent, as already mentioned. Examples of suitable solvents or dispersing agents are those which have been described for carrying out the cyclization, and moreover also, for example, pyridine and amides, such as, for example, dimethylformamide. In addition to water, polar organic solvents, such as dimethylformamide, dimethylsulphoxide or pyridine are preferred for the acylation. Solvent mixtures, such as, for example, a mixture of water and methylene chloride, are also suitable.

The substituted 3-aminosydnonimines of the general formula I form acid addition salts with inorganic or organic acids. Inorganic or organic acids are suitable for the formation of such acid addition salts. Examples of suitable acids are hydrochloric acid, hydrobromic acid, naphthalenedisulphonic acids, in particular naphthalene-1,5-disulphonic acid, and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. Pharmacologically acceptable acid addition salts are preferred. The acid addition salts can be prepared in the customary manner by combining the components, advantageously in a suitable solvent or diluent.

The acid addition salts are usually obtained in the synthesis of the compounds of the formula Ia. If desired, the free compounds of the general formula I or Ia can be obtained from the acid addition salts in a known manner, that is to say by dissolving or suspending in water and rendering the solution or suspension alkaline, for example with sodium hydroxide solution, and subsequently isolating the compounds.

The starting compounds of the general formula II required can be prepared in a manner which is known per se by the Strecker's aminonitrile synthesis from compounds of the general formula IV

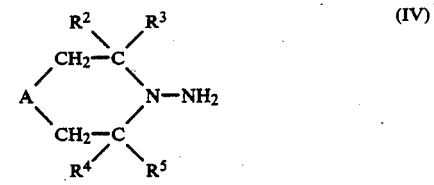

wherein A, $R^2$, $R^3$, $R^4$ and $R^5$ have the meanings already given, by reaction with formaldehyde and hydrocyanic acid or sodium cyanide in a suitable solvent, for example water, a compound of the general formula V

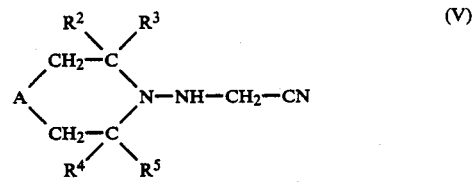

initially being formed and being converted into the compound II by nitrozation. The nitrozation is carried out in a known manner in a suitable solvent, preferably in water, at temperatures of 0° to 10° C. The nitrous acid is thereby usually generated from an alkali metal nitrite, for example sodium nitrite, and hydrochloric acid. It is advantageous to bring the aqueous solution of the compound V to a pH of 1 to 3 with hydrochloric acid and to add the alkali metal nitrite dropwise, in the form of an aqueous solution, to the stirred and cooled solution of the compound.

The solution of the compound II thereby obtained can be subjected directly to the cyclization reaction. Usually, however, it is appropriate for the nitroso compound II first to be taken up in a suitable organic solvent and to carry out the cyclization to give the compound of the formula Ia in this solvent, if appropriate after addition of a further solvent.

The compounds of the general formula IV are known in some cases or can be prepared from compounds of the general formula VI

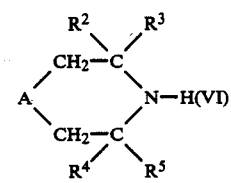

by a process in which either
(a) a compound of the formula VI is nitrosated to give the N-nitroso compound VII and this is then reduced, advantageously with lithiumaluminium hydride:

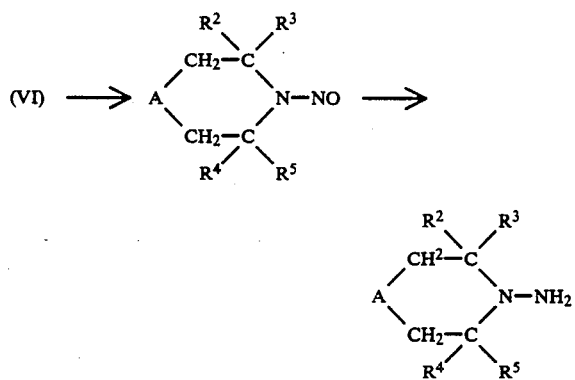

or in a manner which is known per se, (b) a compound of the formula VI is converted into the urea derivative VIII with potassium cyanate in an acid medium, and this derivative is then converted into the compound IV by oxidation with sodium hypochlorite by Hoffmann degradation.

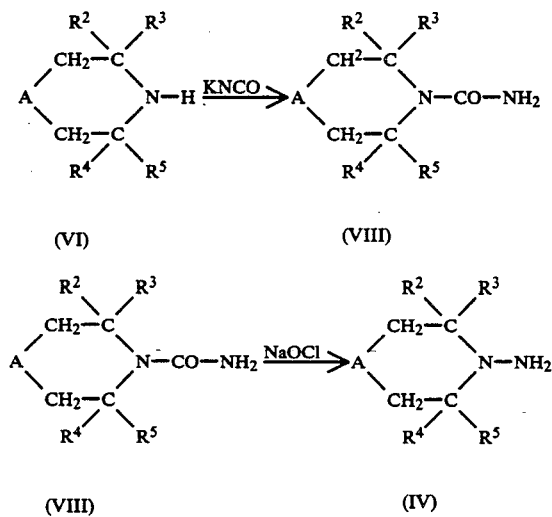

The preparation of the starting compounds of the formulae IV and VI is known. Starting compounds of the formula VI can be prepared, for example, from compounds of the general ulae IX or X

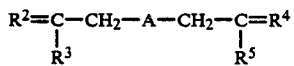

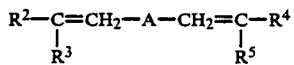

wherein $R^2$ to $R^5$ and A have the meanings already given and which can be prepared by methods which are known per se, by cyclization with ammonia. The reaction with ammonia can be carried out at temperatures of 20° to 150° C., preferably at 60° to 100° C., with or without a solvent.

The preparation of the starting compound IV 1-amino-2,2,6,6-tetramethylpiperidine is described, for example, by J. R. Roberts and K. U. Ingold in J.A.C.S. 95 (1973), 3229 and by William D. Hinsberg III, Peter G. Schultz and Peter B. Dervan in J.A.C.S. 104, (1982), 771, who also describe the preparation of the starting compound 1-amino-2,2,5,5-tetramethylpyrrolidine on page 772. The preparation of the starting compound IV 1-amino-1-aza-2,2,6,6-tetramethyl-4-thiacyclohexane 4,4-dioxide is described in Example 8 of DE-A-2,351,865. 2,2,6,6-Tetraalkyl-substituted 1-aza-4-thiacyclohexane 4,4-dioxides are also described in DE-A-2,351,865. The preparation of 3,3,5,5-tetraalkyl-substituted morpholines as starting compounds IV is described by J. T. Lai in Synthesis (1984), 122–123. Other starting compounds of the formulae IV and VI can be prepared in accordance with instructions analogous to those mentioned above.

The compound of the general formula I and their pharmacologically acceptable acid addition salts have useful pharmacological properties. Their effect on the cardiovascular system is particularly pronounced. Compared with known sydnonimine compounds substituted in the 3-position, for example those of EP-B-59,356, and the commercially available structurally similar compound molsidomine, they surprisingly have a considerably longer duration of action. For example, they reduce the blood-pressure as well as the pulmonary arterial pressure and the left ventricular end-diastolic pressure, and thus contribute towards relieving cardiac activity in the sense of an antianginal action, without thereby provoking reflectory tachycardia.

The compounds of the formula I and their pharmacologically acceptable acid addition salts can therefore be administered to humans as medicines by themselves, in mixtures with one another or in the form of pharmaceutical formulations which permit enteral or parenteral use and contain, as the active constituent, an effective dose of at least one compound of the formula I or of an acid addition salt thereof, alongside customary pharmaceutically acceptable excipients and additives.

The medicines can be administered orally, for example in the form of pills, tablets, lacquered tablets, coated tablets, hard and soft gelatin capsules, solutions, syrups, emulsions or suspensions or aerosol mixtures. However, they can also be administered rectally, for example in the form of suppositories, or parenterally, for example in the form of injection solutions, or percutaneously, for example in the form of ointments or tinctures.

Pharmaceutically inert inorganic or organic excipients can be used to prepare the pharmaceutical preparations. For example, lactose, maize starch or derivatives thereof, talc, stearic acid or salts thereof and the like can be used to prepare pills, tablets, coated tablets and hard gelatin capsules. Excipients for soft gelatin capsules and suppositories are, for example, fats, waxes, semi-solid and liquid polyols, natural or hardened oils and the like. Suitable excipients for the preparation of solutions and syrups are, for example, water, sucrose, invert sugar, glucose, polyols and the like. Suitable excipients for the preparation of injection solutions are, for example, water, alcohols, glycerol, polyols or vegetable oils.

The pharmaceutical preparations can also contain, in addition to the active compounds and excipients, additives, such as, for example, fillers, extenders, disintegrating agents, binders, lubricants, wetting agents, stabilizers, emulsifying agents, preservatives, sweeteners, colouring agents, flavouring agents, aromatizing agents or buffer substances, and furthermore solvents or solubilizing agents or agents for achieving a depot effect, as well as salts for modifying the osmotic pressure, coating agents or antioxidants. They can also contain two or more compounds of the formula I or their pharmacologically acceptable acid addition salts and furthermore other therapeutically active substances.

Examples of such other therapeutically active substances are: β-receptor blockers, such as, for example, propranolol, pindolol and metoprolol; vasodilators, such as, for example, carbochromene; tranquilizers, such as, for example, barbituic acid derivatives, 1,4-benzodiazepines and meprobamate; diuretics, such as, for example, chlorothiazide; agents which tonic the heart, such as, for example, digitalis preparations; antihypertensive agents, such as, for example, hydralazine, dihydralazine, prazosine, clonidine and Rauwolfia alkaloids; agents which reduce the level of fatty acids in the blood, such as, for example, benzafibrate and fenofibrate; and agents for the prophylaxis of thrombosis, such as, for example, phenprocoumon.

The compounds of the formula I, their pharmacologically acceptable acid addition salts and pharmaceutical preparations containing the compounds of the formula I or their pharmacolologically acceptable acid addition salts as active compounds can be used on humans for combating or preventing diseases of the cardiovascular system, for example as antihypertensive medicines for the various forms of high blood pressure, and for combating or preventing angina pectoris and the like. The dosage can vary within wide limits and is to be adapted to suit the individual circumstances in each particular case. A daily dose of about 0.5 to 100 mg, preferably 1 to 20 mg per human individual is in general appropriate for oral administration. Because of the good absorption of the active compounds, the daily dose is also within similar quantity ranges, that is to say in general also 0.5 to 100 mg/person, with other forms of administration. The daily dose is usually divided into several, for example 2 to 4, part administrations.

The pharmacological action of the compounds of the formula I has been determined by a modified method of Godfraind and Kaba (Arch. Int. Pharmacodyn. Ther. 196, (Suppl) 35 to 49, 1972) and of Schüman et al (Naunyn-Schmiedeberg's Arch Pharmacol. 289 409 to 418, 1975). Unless, spiral strips of the arteria pulmonalis of the guinea pig are depolarized with 40 mmol/l of potassium after equilibration in calcium-free tyrode solution. Addition of 0.5 mmol/l of $CaCl_2$ then initiates a contraction. The relaxing action of the test substance is determined by cumulative addition in concentrations in steps of ½ log 10. The concentration of test substance which inhibits the contraction by 50% (=$IC_{50}$, mol/l) is determined from the concentration/effects curve (abscissa: —log mol/l of test substance, ordinate: % inhibition of the maximum concentration, mean value of 4 to 6 strips of vessel). The $IC_{50}$ values thus obtained are shown in the following table. As the comparison with the $IC_{50}$ value of $3 \times 10^{-4}$ for the known compound molsidomine (N-ethoxycarbonyl-3-morpholinosydnonimine), compare No. DE-B-1,695,897, shows, the values for the compounds of the formula I are considerably more favourable.

| $IC_{50}$ values in mol/l | $IC_{50}$ |
|---|---|
| a 3-(2,2,6,6-Tetramethylpiperidino)-sydnonimine hydrochloride | $3 \times 10^{-5}$ |
| b 3-(2,2,6,6-Tetramethyl-4-isopropyl-piperazin-1-yl)sydnonimine dihydrochloride | $3 \times 10^{-6}$ |
| c 3-(3,3,5,5-Tetramethylmorpholino)-sydnonimine hydrochloride | $1 \times 10^{-4}$ |

| $IC_{50}$ values in mol/l | $IC_{50}$ |
|---|---|
| d N-Ethoxycarbonyl-3-morpholinosydnonimine | $3 \times 10^{-4}$ | a to c: compounds according to the invention
d: comparison compound molsidomine

EXAMPLE 1

3-(2,2,6,6-Tetramethylpiperidino)sydnonimine hydrochloride (a) N-(2,2,6,6-Tetramethylpiperidino)aminoacetonitrile A solution of 8.7 g of potassium cyanide in 20 ml of water is added to an ice-cooled mixture of 17.5 g of 1-amino-2,2,6,6-tetramethylpiperidine, 11 g of concentrated hydrochloric acid and 50 ml of water, and the pH is brought to 6.5 with hydrochloric acid. 9.5 g of a 39% aqueous formaldehyde solution are then added and the reaction mixture is stirred at 0° C. for 3 hours and at room temperature for a further 3 hours. The product is extracted with ethyl acetate and the ethyl acetate phase is washed with dilute glacial acetic acid and dried over sodium sulphate. After concentration, a slightly crystalline residue of 10.7 g of N-(2,2,6,6-tetramethylpiperidino)aminoacetonitrile remains and is further processed without additional purification.

(b) 3-(2,2,6,6-Tetramethylpiperidino)sydnonimine hydrochloride

A solution of 4.2 g of sodium nitrite in 10 ml of water is added dropwise to a mixture of 10.7 g of the compound described above under (a), 50 ml of water, 50 ml of ethyl acetate and 6 g of concentrated hydrochloric acid, and after the mixture has been stirred at room temperature for 5 hours the organic phase is separated off, diluted with 15 ml of methanol and stirred in an ice-bath. After excess hydrogen chloride has been passed in, the mixture is subsequently stirred at room temperature for 15 hours and concentrated in a water pump vacuum. The residue crystallizes when stirred with deithyl ether. It is filtered off with suction and washed with ethyl acetate.

Yield: 8.6 g of 3-(2,2,6,6-tetramethylpiperidino)sydnonimine hydrochloride of melting point: 170° C. (decomposition).

EXAMPLE 2

3-(2,2,6,6-Tetramethylpiperidino)-N-ethoxycarbonyl sydnonimine 3.5 g of sodium bicarbonate are added to an ice-cooled solution of 5 g of 3-(2,2,6,6-tetramethylpiperidino)sydnonimine hydrochloride according to Example 1 b) in 20 ml of water, a solution of 2.5 g of ethyl chloroformate in 20 ml of methylene chloride is then added and the mixture is stirred at room temperature for 4 hours. The organic phase is separated off, dried and concentrated. The residue is triturated with petroleum ether and filtered off with suction.

Yield: 4.2 g of 3-(2,2,6,6-tetramethylpiperidino)-N-ethoxycarbonylsydnonimine of melting point 74 to 75° C.

EXAMPLE 3

3-(3,3,5,5-Tetramethylmorpholino)sydnonimine hydrochloride

(a) 4-Nitroso-3,3,5,5-tetramethylmorpholine 15.6 g of sodium nitrite are added to a solution of 27 g of 3,3,5,5-tetramethylmorpholine hydrochloride (prepared in accordance with Synthesis (1984), 122) in 80 ml of water and the mixture is heated at 80° C. for 3 hours. After cooling, the nitroso compound is extracted with diethyl ether. After drying and concentration of the ether phase, 22.2 g of the compound crystallize out. Melting point: 47° C.

(b) 4-Amino-3,3,5,5-tetramethylmorpholine

About 20% of a solution of 5 g of lithium alanate in 50 ml of tetrahydrofuran is added dropwise to a heated solution of 17.2 g of 4-nitroso-3,3,5,5-tetramethylmorpholine in 50 ml of tetrahydrofuran and 100 ml of dibutyl ether. The tetrahydrofuran is distilled off and the internal temperature is increased to 99° C. The remainder of the lithium alanate solution is then added dropwise and the mixture is kept at 70° C. for a further hour. After the mixture has been cooled in an ice-bath, 10 ml of water and 10 ml of 15% strength sodium hydroxide solution are carefully added. After filtration with suction, the filtrate is extracted by shaking first with water and then with 100 ml of 1N hydrochloric acid. The aqueous HCl phase is then extracted by shaking once more with diethyl ether and used in the next stage.

(c) N-(3,3,5,5-Tetramethylmorpholino)aminoacetonitrile

A solution of 8.7 g of potassium cyanide in 20 ml of water is added to the HCl phase from the preceding stage and the pH is brought to 6.5 with hydrochloric acid. 9.5 g of a 39% strength aqueous formaldehyde solution are then added and the reaction mixture is stirred at 0° C. for 3 hours and at room temperature for a further 3 hours. The product is extracted with ethyl acetate and the ethyl acetate phase is washed with dilute glacial acetic acid and dried over sodium sulphate. After concentration, a partly crystalline residue of N-(3,3,5,5-tetramethylmorpholino)aminoacetonitrile remains and is further processed without additional purification.

(d) 3-(3,3,5,5-Tetramethylmorpholino)sydnonimine hydrochloride

A solution of 4.2 g of sodium nitrite in 10 ml of water is added dropwise to a mixture of the compound described above under (c), 50 ml of water, 50 ml of ethyl acetate and 6 g of concentrated hydrochloric acid and, after stirring at room temperature for 5 hours, the organic phase is separated off, diluted with 15 ml of methanol and stirred in an ice-bath. After excess hydrogen chloride has been passed in, the mixture is subsequently stirred at room temperature for 15 hours and concentrated in a water pump vacuum. The residue crystallizes when stirred with diethyl ether. It is filtered off with suction and washed with ethyl acetate.

Yield: 3.9 g of 3-(3,3,5,5-tetramethylmorpholino)sydnonimine hydrochloride of melting point: 132–133° C. (decomposition).

EXAMPLE 4

3-(2,2,6,6-Tetramethyl-4-isopropylpiperazin-1-yl)sydnonimine dihydrochloride

(a) 1-Nitroso-2,2,6,6-tetramethyl-4-isopropylpiperazine 15.6 g of 1-isopropyl-3,3,5,5-tetramethylpiperazine are reacted analogously to the instructions of Example 3a. Working up with 14 8 g of an oil.

(b) 1-Amino-2,2,6,6-tetramethyl-4-isopropylpiperazine

The 1-nitroso-2,2,6,6-tetramethyl-4-isopropylpiperazine obtained in the preceding stage is reacted analogously to 3b. The resulting aqueous HCl phase is used in the next stage.

(c) N-(2,2,6,6-Tetramethyl-4-isopropylpiperazin-1-yl)aminoacetonitrile

The aqueous HCl phase from the preceding stage is further processed analogously to Example 3c and the product thereby obtained is used in the following stage.

(d) 3-(2,2,6,6-Tetramethyl-4-isopropylpiperazin-1-yl)sydnonimine dihydrochloride The product obtained in the preceding stage is further processed analogously to Example 3(d).

Yield: 4.6 g of 3-(2,2,6,6-tetramethyl-4-isopropylpiperazino)sydnonimine dihydrochloride of melting point 142° C. (decomposition).

(e) 1-Isopropyl-3,3,5,5-tetramethylpiperazine

The 1-isopropyl-3,3,5,5-tetramethylpiperazine required as the starting substance in stage (a) can be prepared as follows:

3.9 g (0.103 mol) of lithiumaluminium hydride are introduced into 100 ml of anhydrous tetrahydrofuran under a nitrogen atmosphere, while stirring and cooling. A solution of 19.8 g (0.1 mol) of 1-isopropyl-3,3,5,5-tetramethyl-2-piperazinone (obtainable, for example, in accordance with Synthesis 1981, page 40, or J. Organ. Chem., 45 (1980), 754–59) in 75 ml of anhydrous tetrahydrofuran is added dropwise at room temperature, whereupon the reaction temperature rises to 6020 C. The mixture is then stirred overnight at room temperature. After dropwise addition of about 10 ml of water, the mixture is subsequently stirred for 2 hours and the precipitate is then filtered off with suction. The filtrate is dried over potassium carbonate and concentrated in vacuo and the crude product which remains as a colourless oil is further processed without additional purification.

Yield: 16 g; $n_D^{25}$ 1 4497.

The other starting substances required can also be prepared analogously.

EXAMPLE 5

3-(3,3,5,5-Tetramethyl-1,4-thiazin-(1,1-dioxide)-4-yl)sydnonimine hydrochloride The compound is prepared analogously to Example 3 starting from 18 g of 4-amino-3,3,5,5-tetramethyl-1,4-thiazin1,1-dioxide (prepared according to Example 8 of DE-A-2,351,865).

Yield: 6.2 g of 3-(3,3,5,5-tetramethyl-1,4-thiazin-1,1-dioxide-4yl)sydnonimine hydrochloride of melting point 177° C. (decomposition).

EXAMPLE 6

3-(2,2,6,6-Tetramethyl-4-isopropylpiperazin-1-yl)sydnonimine hydrochloride

The compound is prepared analogously to Example 4

Melting point: 110°-112° C. (decomposition).

EXAMPLE 7

3-(2,2,6,6-Tetramethyl-4-(2-hydroxy-1,1-dimethylethyl)piperazin-1-yl)sydnonimine hydrochloride The compound is prepared analogously to Example 4.

Melting point: 124°-126° C. (decomposition).

EXAMPLE 8

3-(2,2,6,6-Tetramethyl-4-benzylpiperazin-1-yl)sydnonimine hydrochloride

The compound is prepared analogously to Example 4.

Melting point: 156°-158° C. (decomposition).

EXAMPLE 9

3-(2,2,6,6-Tetramethyl-4-isopropylpiperazin-1-yl)-N-ethoxycarbonylsydnonimine

The compound is prepared analogously to Example 2.

Melting point: 98°-99° C. (decomposition).

3,3,5,5-Tetraalkyl-substituted piperazines can be prepared, for example, by the process described in example 4e.

EXAMPLE 10

3-(2,2,6,6-Tetramethyl-4-isopropylpiperzin-1-yl)-N-acetylsydnonimine

The compound is prepared analogously to Example 2.

Melting point: 121°-123° C. (decomposition).

EXAMPLE 11

3-(2,2,6,6-Tetramethyl-4-isopropylpiperazin-1-yl)-N-benzoylsydnonimine

The compound is prepared analogously to Example 2.

Melting point: 133°-135° C. (decomposition).

EXAMPLE 12

3-(2,2,6,6-Tetramethylpiperidino)-N-cyclohexylcarbonylsydnonimine

The compound is prepared analogously to Example 2.

Melting point: 107°-108° C. (decomposition).

EXAMPLE 13

3-(3,3,5,5-Tetramethylmorpholino)-N-isobutyrylsydnonimine

The compound is prepared analogously to Example 2.

Melting point: 88°-89° C. (decomposition).

Pharmaceutical preparations are described in the following examples A to E.

EXAMPLE A

Soft gelatin capsules containing 5 mg of active compound per capsule.

|  | per capsule |
|---|---|
| Active compound | 5 mg |
| Fractionated triglyceride mixture from coconut oil | 150 mg |
| Capsule contents | 155 mg |

EXAMPLE B

Injection solution containing 1 mg of active compound per ml:

|  | per ml |
|---|---|
| Active compound | 1.0 mg |
| Polyethylene glycol 400 | 0.3 ml |
| Sodium chloride | 2.7 mg |
| Water for injection purposes to | 1 ml |

EXAMPLE C

Emulsion containing 3 mg of active compound per 5 ml

|  | per 100 ml of emulsion |
|---|---|
| Active compound | 0.06 g |
| Neutral oil | q.s. |
| Sodium carboxymethylcellulose | 0.6 g |
| Polyoxyethylene stearate | q.s. |
| Glycerol, pure | 0.2 to 2.0 g |
| Flavour substance | q.s. |
| Water (demineralized or distilled) to | 100 ml |

EXAMPLE D

Rectal drug form containing 4 mg of active compound per suppository

|  | per suppository |
|---|---|
| Active compound | 4 mg |
| Suppository base mass to | 2 g |

EXAMPLE E

Tablets containing 2 mg of active compound per tablet

|  | per tablet |
|---|---|
| Active compound | 2 mg |
| Lactate (finely ground) | 2 mg |
| Maize starch (white) | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl starch | 25 mg |
|  | 311 mg |

While there has been described herein what are at present considered to be the preferred embodiments of the present invention, it will be obvious to those skilled in the art that various changes and modifications may be made without departing from the invention, and it is, therefore, aimed in the appended claims to cover all such changes and modifications as fall within the true spirit and scope of the invention.

We claim:

1. A substituted 3-aminosydnonimine of the formula I

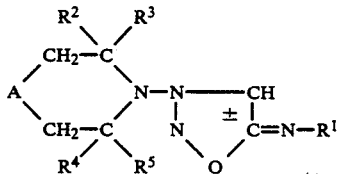

or a pharmaceutically acceptable acid addition salt thereof, wherein

A denotes the radical —CH$_2$—, —O—S(O)$_n$—, —N(R$^6$)— or a direct bond,

R$^1$ denotes hydrogen or the radical —COR$^7$;

R$^2$, R$^3$, R$^4$, and R$^5$ denote identical or different C$_{1-4}$ alkyl;

n denotes a number 0, 1 or 2;

R$^6$ denotes alkyl with 1 to 4 C atoms; hydroxyalkyl with 2 to 4 C atoms; or phenylalkyl with 1 to 4 C atoms in the alkyl radical, R$^7$ denotes C$_{1-4}$ alkyl which can also be substituted by alkoxy with 1 to 3 C atoms; C$_{5-7}$ cycloalkyl; pinan-3-yl; adamantyl; an alkoxy radical with 1 to 6 C atoms; phenoxy; α-naphthoxy; β-naphthoxy; an alkoxycarbonyl radical with a total of 2 to 7 C atoms; phenyl; α-naphthyl; β-naphthyl; phenyl or α- or β-naphthyl mono-, di- or trisubstituted by 1 to 3 haloqen atoms and/or 1 to 3 alkyl radicals with 1 to 3 C atoms and/or 1 to 3 alkoxy radicals with 1 to 3 C atoms and/or 1 to 2 nitro groups;

2. Substituted 3-aminosyldnonimines according to claim 1, characterized in that R$^1$ denotes hydrogen.

3. Substituted 3-aminosydnonimines according to claim 1, characterized in that R$^2$, R$^3$, R$^4$ and R$^5$ denote methyl.

4. Substituted 3-aminosydnonimines according to claim 1, characterized in that A denotes —CH$_2$—, —O— or —N(R$^6$)—.

5. 3-(2,2,6,6-Tetrtamethylpiperidino)sydnonimine or its pharmacologically acceptable acid addition salt.

6. 3-(2,2,6,6-Tetramethyl-4-isopropylpiperazin-1-yl)sydnonimine or its pharmaceutically acceptable acid addition salt.

7. Pharmaceutical preparation for combating or preventing high blood pressure and/or angina pectoris, characterized in that it contains an effective amount of a compound of claim 1 or a pharmaceutically acceptable acid addition salt thereof as the active compound, together with pharmaceutically acceptable excipients and additives and, optionally, one or more other pharmaceutically active compounds.

8. A method for treating angina pectoris and/or high blood pressure which comprises administering an effective dose of a pharmaceutical preparation according to claim 1 to a host afflicted with or subject to one or more of such conditions.

9. 3-(2,2,6,6-tetramethyl-4-isopropylpiperazine-1-yl)sydnonimine dihydrochloride.

* * * * *

UNITED STATES PATENT AND TRADEMARK OFFICE
CERTIFICATE OF CORRECTION

PATENT NO. : 4,937,244

DATED : June 26, 1990

INVENTOR(S) : Karl Schonafinger et al.

It is certified that error appears in the above-identified patent and that said Letters Patent is hereby corrected as shown below:

Column 15, line 14, "-O-S(O) -" should read -- -O-, -S(O) - --;
Column 16, line 2,(claim 1, last line), ";" should read --.--
Column 16, line 15, "yl)sydnonimine" should read -- yl)-sydnonimine --.

Signed and Sealed this

Second Day of July, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,937,244

DATED : June 26, 1990

INVENTOR(S) : Schonafinger et al.

It is certified that error appears in the above-identified patent and that said Letters Patent is hereby corrected as shown below:

On the title page, item [75] should read as follows:

[75] Inventors: Karl Schönafinger, Alzenau;
Rudi Beyerle, Frankfurt;
Helmut Bohn, Schöneck, and
Melitta Just, Nidderau,
all of the Federal Republic of Germany Signed and Sealed this Sixth Day of October, 1992

*Attest:*

DOUGLAS B. COMER

*Attesting Officer*    *Acting Commissioner of Patents and Trademarks*

UNITED STATES PATENT AND TRADEMARK OFFICE
CERTIFICATE OF CORRECTION

PATENT NO. : 4,937,244
DATED : June 26, 1990
INVENTOR(S) : Karl Schonafinger et al It is certified that error appears in the above-identified patent and that said Letters Patent is hereby corrected as shown below:

Column 15, line 14, "-O-S(O)$_n$-" should read -- -O-, -S(O)$_n$- --.
Column 16, line 2, (claim 1, last line), ";" should read --.--;
Column 16, line 15, "yl)sydnonimine" should read -- yl)-sydnonimine --.

This certificate supersedes Certificate of Correction issued July 2, 1991.

Signed and Sealed this

First Day of December, 1992

Attest:

DOUGLAS B. COMER

Attesting Officer    Acting Commissioner of Patents and Trademarks